United States Patent
Pagot et al.

(10) Patent No.: US 11,242,301 B2
(45) Date of Patent: Feb. 8, 2022

(54) METHOD OF HYDROGENOLYSIS FOR IMPROVED PRODUCTION OF PARAXYLENE

(71) Applicant: IFP Energies Nouvelles, Rueil-Malmaison (FR)

(72) Inventors: Alexandre Pagot, Saint Genis Laval (FR); Denis Uzio, Saint Genis Laval (FR); Jean-Francois Joly, Lyons (FR); Anne-Claire Dubreuil, Lyons (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 16/631,887

(22) PCT Filed: Jul. 16, 2018

(86) PCT No.: PCT/EP2018/069243
§ 371 (c)(1),
(2) Date: Jan. 17, 2020

(87) PCT Pub. No.: WO2019/016127
PCT Pub. Date: Jan. 24, 2019

(65) Prior Publication Data
US 2020/0148611 A1    May 14, 2020

(30) Foreign Application Priority Data
Jul. 20, 2017    (FR) ..................... 1756905

(51) Int. Cl.
C07C 4/12    (2006.01)
C07C 6/12    (2006.01)
(Continued)

(52) U.S. Cl.
CPC ............... *C07C 6/126* (2013.01); *C07C 4/12* (2013.01); *C07C 5/2702* (2013.01); *C07C 15/08* (2013.01); *C07C 2523/755* (2013.01)

(58) Field of Classification Search
None
See application file for complete search history.

(56) References Cited

U.S. PATENT DOCUMENTS 4,320,242 A * 3/1982 Onodera .................. C07C 4/18
                                                           208/111.15
5,409,595 A    4/1995 Harandi et al.
(Continued)

FOREIGN PATENT DOCUMENTS

PL        178539 B1     5/2000
WO      9505351 A1     2/1995
(Continued)

OTHER PUBLICATIONS

Machine Translation of WO 2017/063558 A1 obtained from Espacenet, pp. 1-17 (Year: 2021).*
(Continued)

*Primary Examiner* — Philip Y Louie
(74) *Attorney, Agent, or Firm* — Millen White Zelano and Branigan, PC; Csaba Henter

(57) ABSTRACT

The invention relates to a selective hydrogenolysis method for treating a feed rich in aromatic compounds having more than 8 carbon atoms, comprising transforming at least one alkyl group with at least two carbon atoms (ethyl, propyl, butyl, isopropyl, etc.) attached to a benzene ring into at least one methyl group. The invention also relates to the integration of the hydrogenolysis unit into an aromatic complex.

16 Claims, 2 Drawing Sheets

(51) Int. Cl.
*C07C 5/27* (2006.01)
*C07C 15/08* (2006.01)

(56) References Cited

U.S. PATENT DOCUMENTS

| | | | |
|---|---|---|---|
| 10,071,939 B2 | 9/2018 | Abudawoud | |
| 2012/0271084 A1* | 10/2012 | Haizmann | C07C 6/126 585/323 |
| 2014/0316174 A1* | 10/2014 | D'Acosta | C07C 2/66 585/24 |
| 2016/0318004 A1* | 11/2016 | Li | B01J 35/023 |
| 2019/0359542 A1* | 11/2019 | Detjen | B01J 29/48 |

FOREIGN PATENT DOCUMENTS

| | | |
|---|---|---|
| WO | 09008876 A1 | 1/2009 |
| WO | 13158956 A1 | 10/2013 |
| WO | WO-2017063558 A1 * 4/2017 | B01J 23/00 |

OTHER PUBLICATIONS

C Hoang-Van et al: "Hydrogenolysis of ethylbenzene over a supported nickel catalyst derived from nickel hydroaluminate", Journal of Catalysis, Jan. 1, 1987 (Jan. 1, 1987), pp. 469-477.

Kim Chong Uk et al.: "Kinetics of ethylbenzene hydrogenolytic dealkylation on Ni-Al2O3 catalyst", Collection Symposium Series (Xiiith Symposium on Chemistry of Nucleic Acid Components Spindleruv Mlyn, Czech Republic; Sep. 3-9, 2005), vol. 54, No. 2, Jan. 1, 1989 (Jan. 1, 1989), XX, pp. 316-320, XP055481785, ISSN: 0010-0765, ISBN: 978-80-86241-25-8, DOI: 10.1135/cccc19890316.

L. Beranek et al.: "Catalytic dealkylation of alkylaromatic compounds. XIV. The effect of structure of monoalkylbenzenes on their reactivity in hydrodealkylation on a nickel catalyst", Collection Symposium Series (XIIITH Symposium On Chemistry of Nucleic Acid Components Spindleruv Mlyn, Czech Republic; Sep. 3-9, 2005), vol. 31, No. 2, Jan. 1, 1966 (Jan. 1, 1966), XX, pp. 566-575, XP055482603, ISSN: 0010-0765, ISBN: 978-80-86241-25-8.

Qunbing Shen et al: "Hydrodealkylation of C9 + Heavy Aromatics to BTX over Zeolite-Supported Nickel Oxide and Molybdenum Oxide Catalysts", Catalysis Letters, Kluwer Academic Publishers-Plenum Publishers, NE, vol. 129, No. 1-2, Jan. 9, 2009 (Jan. 9, 2009), pp. 170-180, XP019672034, ISSN: 1572-879X.

T. Jin et al: "The Effect of Metal Introduced Over ZSM-5 Zeolite for C 9 Heavy Aromatics Hydrodealkylation", Petroleum Science and Technology, vol. 27, No. 16, Sep. 30, 2009 (Sep. 30, 2009), US, pp. 1821-1835, XP055481529, ISSN: 1091-6466.

International Search report PCT/EP2018/069243 dated Sep. 28, 2018 (pp. 1-8).

* cited by examiner

METHOD OF HYDROGENOLYSIS FOR IMPROVED PRODUCTION OF PARAXYLENE

CONTEXT OF THE INVENTION

The invention relates to the conversion of aromatics in the context of the production of aromatics for the petrochemical industry (benzene, toluene, PX, OX). The aromatic complex is fed with C6 to C10+ feedstocks, originating from reformate, the effluent from the catalytic reforming of gasolines. The alkylaromatics are extracted therefrom and then converted into desired intermediates. The products of interest are aromatics with 0, 1 or 2 methyl groups, xylenes having the greatest market value. It is thus appropriate to have available methyl groups.

The subject matter of the invention is a process for the selective hydrogenolysis of C2+ alkyl chains, in order to convert them into methyl groups. This unit can:
- either be used on feedstocks upstream of the aromatic complex, in order to pretreat them and to produce entities having between 6 and 10 carbon atoms and predominantly or exclusively containing alkyls of methyl types.
- or be integrated into the aromatic complex in order to treat certain fractions. Generally, the C9/C10 fraction is converted in a transalkylation unit, one of the catalysts of which makes it possible, by acid catalysis, to dealkylate the long chains flush with the nucleus. One of the objectives of the present process is to retain the final carbon, in order to produce methyls and thus to maximize the production of xylenes.

EXAMINATION OF THE PRIOR ART

Figure 1:
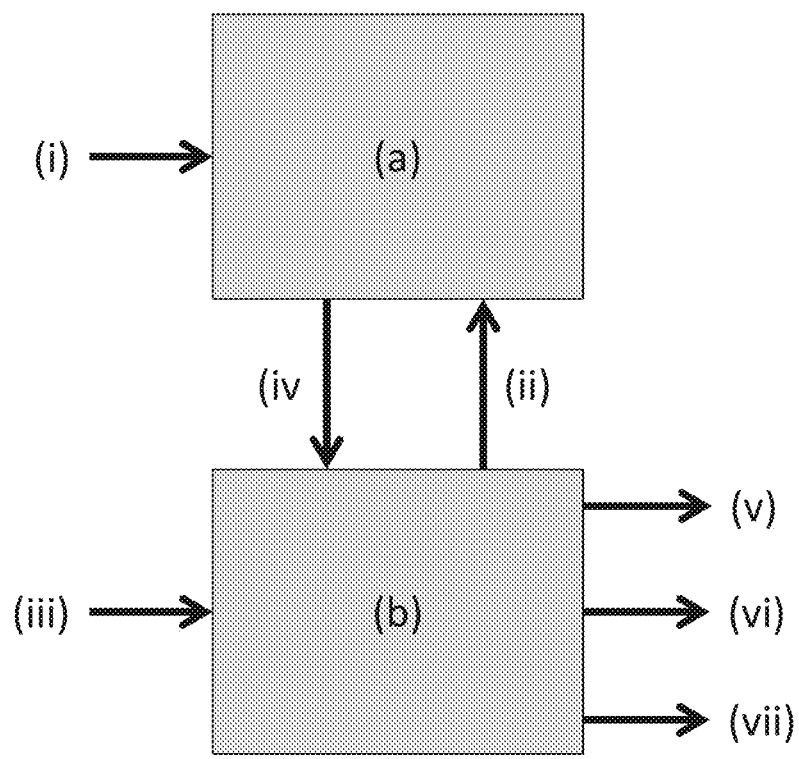
FIG. 1 according to the invention is a diagrammatic view of the hydrogenolysis unit (a) according to the invention and of an "aromatic complex" unit (b), the two units having exchanges between them symbolized by the streams (IV) and (II).

To date, aromatic complexes make it possible to produce benzene, optionally toluene, and xylenes (often para-xylene, denoted PX, sometimes ortho-xylene, denoted OX). An aromatic complex generally has available the following catalytic units:
- Isomerization of the A8s. This unit makes it possible to convert the OX and the MX into PX and, for some, to also convert ethylbenzene into xylenes by isomerization.
- Transalkylation; starting from a mixture of benzene, toluene, trimethylbenzenes and tetramethylbenzene, the unit produces xylenes.

All the alkyl chains having more than two carbon atoms (C2+) thus have to be treated (except, in certain cases, ethylbenzene). Within the aromatic complex, this function is provided by acid catalysis, which makes it possible to cut the alkyls flush with the nucleus (reaction known as "paring reaction"). All the carbons of the C2+ alkyls are then lost.

There also exist units for the hydrodealkylation of alkylaromatics for producing benzene, which do not exhibit any selectivity, the aim being to retain only the aromatic nucleus in order to produce benzene. These units are based on metal catalysis and require severe temperature and $H_2$ pressure (generally greater than 25 bar) conditions. Mention may be made, as reference, of the patents: GB 999 860 and GB 790 595. In all cases, the temperatures claimed are greater than 500° C., predominantly above 593° C.

The document which may be regarded as the closest prior art to the present invention is the patent U.S. Pat. No. 2,438,570. This document describes a process for the dealkylation of monoalkylated aromatic compounds which makes it possible to carry out a cleavage between the carbon in the α position and the carbon in the β position, so as to retain only a methyl group. Also found in this document is the notion of selectivity with a predominant production of toluene from ethylbenzene, particularly in example 3 of the cited document.

The invention consists of a process for the selective hydrogenolysis of alkylaromatics and its integration within an aromatic complex, in order to maximize the production of para-xylene.

BRIEF DESCRIPTION OF THE INVENTION

The present invention can be defined as a selective hydrogenolysis process in which a feedstock rich in aromatic compounds having more than 8 carbon atoms is treated and which consists in converting one or more alkyl group(s) having at least two carbon atoms (ethyl, propyl, butyl, isopropyl and the like groups) attached to a benzene nucleus into one or more methyl group(s), that is to say formed of a $CH_3$ group alone. The hydrogenolysis process according to the present invention is carried out in the presence of a catalyst comprising at least one metal from Group VIII of the Periodic Table, preferably nickel or platinum, deposited on a porous support comprising at least one crystalline or noncrystalline refractory oxide, having or not having structured porosity.

The reaction takes place under the following operating conditions:
- at a temperature of between 300° C. and 550° C., preferentially of between 350° C. and 500° C., and more preferentially still of between 370° C. and 450° C.,
- at a pressure of between 1 and 30 bar, preferentially of between 2 and 20 bar, and more preferentially still of between 2 and 10 bar,
- with a $H_2$/HC molar ratio of between 1 and 10, and preferentially of between 1.5 and 6,
- with an HSV of between 0.1 and 50 $h^{-1}$, preferentially of between 1 and 30 $h^{-1}$ and more preferentially still of between 3 and 20 $h^{-1}$.

According to a first alternative form of the selective hydrogenolysis process according to the invention, the hydrogenolysis reactor used in said process is of fixed bed type and the catalyst support is provided in the form of extrudates.

According to a second alternative form of the selective hydrogenolysis process according to the present invention, the reactor is of moving bed type and the catalyst support is provided in the form of approximately spherical beads. A moving bed is generally defined as a gravity flow bed, such as those encountered in the catalytic reforming of gasolines.

The hydrocarbon feedstock of the hydrogenolysis process according to the invention generally contains more than 80% by weight of aromatics, and the aromatic molecules having between 8 and 10 carbon atoms represent at least 90% by weight of the feedstock.

According to the present invention, the hydrogenolysis process can be integrated in a process for the production of xylenes using an aromatic complex, said aromatic complex being characterized in that it contains at least:

a unit for the hydrogenolysis of alkylaromatics in which aromatics having between 9 and 10 carbon atoms, imported or extracted from internal streams of the aromatic complex, are treated, a unit of transalkylation type in which a part of the toluene and of the trimethylbenzenes is converted into xylenes; advantageously, this unit can also treat tetramethylbenzenes and, to a certain extent, benzene, a fractionation train which makes it possible to extract the xylenes from the other aromatics, a unit for the separation of xylenes which makes it possible to isolate para-xylene, an optional unit for the isomerization of the raffinate obtained as effluent from the unit for the separation of the xylenes.

The process for the production of xylenes according to the invention, that is to say integrating a selective hydrogenolysis unit (a1), has a fractionation train comprising columns for distillation (e), (f), (g) and (h) of the aromatic compounds which makes it possible to separate the following 5 fractions:

a benzene fraction
a toluene fraction
an aromatic fraction having 8 carbon atoms (xylenes and ethylbenzene)
an aromatic fraction having 9 and 10 carbon atoms
a heavy aromatics fraction, the most volatile entities of which are aromatics having 10 carbon atoms.

The selective hydrogenolysis unit (a1) forming part of the aromatic complex treats the aromatic fraction having 9 and 10 carbon atoms resulting from the fractionation train and an imported feedstock rich in alkylaromatics. The effluents are then separated. The heavy fraction of the effluents having more than 9 carbon atoms is mixed with the toluene fraction resulting from the fractionation train. This mixture feeds the transalkylation unit (k1). The light fraction having 8 and fewer carbon atoms (A8−) is recycled to the fractionation train.

In some cases, this aromatic fraction having 8 and fewer carbon atoms (A8−) can be treated in a unit for the extraction of para-xylene (i).

The unit for the extraction of para-xylene (i) forming part of the aromatic complex can be of simulated moving bed type then using a molecular sieve and a desorbent.

The raffinate resulting from the unit for the extraction of para-xylene (i), essentially formed of ortho-xylene, meta-xylene and ethylbenzene, can be converted in an isomerization unit (j1) targeted at producing para-xylene, the effluents of which are recycled to the fractionation train.

DETAILED DESCRIPTION OF THE INVENTION

The objective of the selective hydrogenolysis unit according to the present invention is to produce methyl groups instead of and in place of alkyl groups having more than two carbon atoms. When the production of xylenes is targeted, benzene is also produced, which corresponds to the amount of aromatic nuclei "in excess", that is to say for which methyl groups are no longer available to produce xylenes. The losses are extremely low and the amount of xylenes is thus, to the first order, conditioned by the number of available methyl groups (n denoting the number of moles):

$$n_{xylene\ at\ the\ outlet} = \frac{n_{methyl\ at\ the\ outlet}}{2}$$

$$n_{benzene\ at\ the\ outlet} = n_{nucleus\ at\ the\ inlet} - n_{xylene\ at\ the\ outlet}$$

The unit of the present invention makes it possible to increase the amount of available methyl groups and consequently the production of xylenes to the detriment of benzene.

The conversion takes place in a reactor of fixed bed or moving bed type, the conditions of which are as follows:

pressure of between 1 and 30 bar, preferentially 2 and 20 bar, preferentially 2 and 10 bar, temperature of between 300° C. and 550° C., preferentially of between 350° C. and 500° C., more preferentially still of between 370° C. and 450° C., $H_2$/HC molar ratio of between 1 and 10, and preferentially of between 1.5 and 6, HSV of between 0.1 and 50 $h^{-1}$, preferentially between 1 and 30 $h^{-1}$, more preferably between 3 and 20 $h^{-1}$.

A detailed description of the catalyst used to carry out the hydrogenolysis reaction can be found in the documents FR 2 963 344 and FR 2 927 267.

The hydrogenolysis catalysts are generally based on metals from Group VIII of the Periodic Table, preferably platinum or nickel. The metal is provided in the form of metal nanoparticles deposited on a support which can be a refractory oxide in the form of beads or extrudates or in forms exhibiting other geometries.

The content of metal from Group VIII is generally of between 0.01% and 50% by weight of said element, preferably between 0.05% and 30% by weight of the mass of the catalyst.

Preferably, the platinum content in the catalyst is generally of between 0.01% and 5% by weight, more preferably still between 0.02% and 3.0% by weight, preferably between 0.05% and 0.6% by weight, of the mass of the catalyst.

More preferably still, the nickel content is generally of between 1% and 50% by weight, preferably between 2% and 20% by weight and more preferably still between 3% and 15% by weight of the mass of the catalyst.

The porous support present in the catalyst of the process of the invention generally comprises at least one crystalline or noncrystalline refractory oxide, having or not having structured porosity, which is generally selected from the oxides of metals from Groups 2, 3, 4, 13 and 14 of the new Periodic Table of the Elements, such as, for example, oxides of magnesium, aluminum, silicon, titanium, zirconium or thorium, taken alone or as a mixture with one another, or as a mixture with other oxides of metals of the Periodic Table.

Charcoal can also be used. The preferred support is chosen from aluminas, silicas or silicas/aluminas and more preferably still it is an alumina or a silica.

The pore volume of the support is generally of between 0.1 and 1.5 $cm^3$/g, preferably of between 0.5 and 1 $cm^3$/g.

The specific surface of the support is generally greater than 5 $m^2$/g, preferably of between 40 and 500 $m^2$/g, more preferably still between 60 and 350 $m^2$/g and more preferably still between 40 and 180 $m^2$/g.

Said porous support is advantageously provided in the form of beads, of extrudates, of pellets or of irregular and nonspherical agglomerates, the specific shape of which can result from a crushing stage. Very advantageously, said support is provided in the form of beads or of extrudates.

Figure 2:
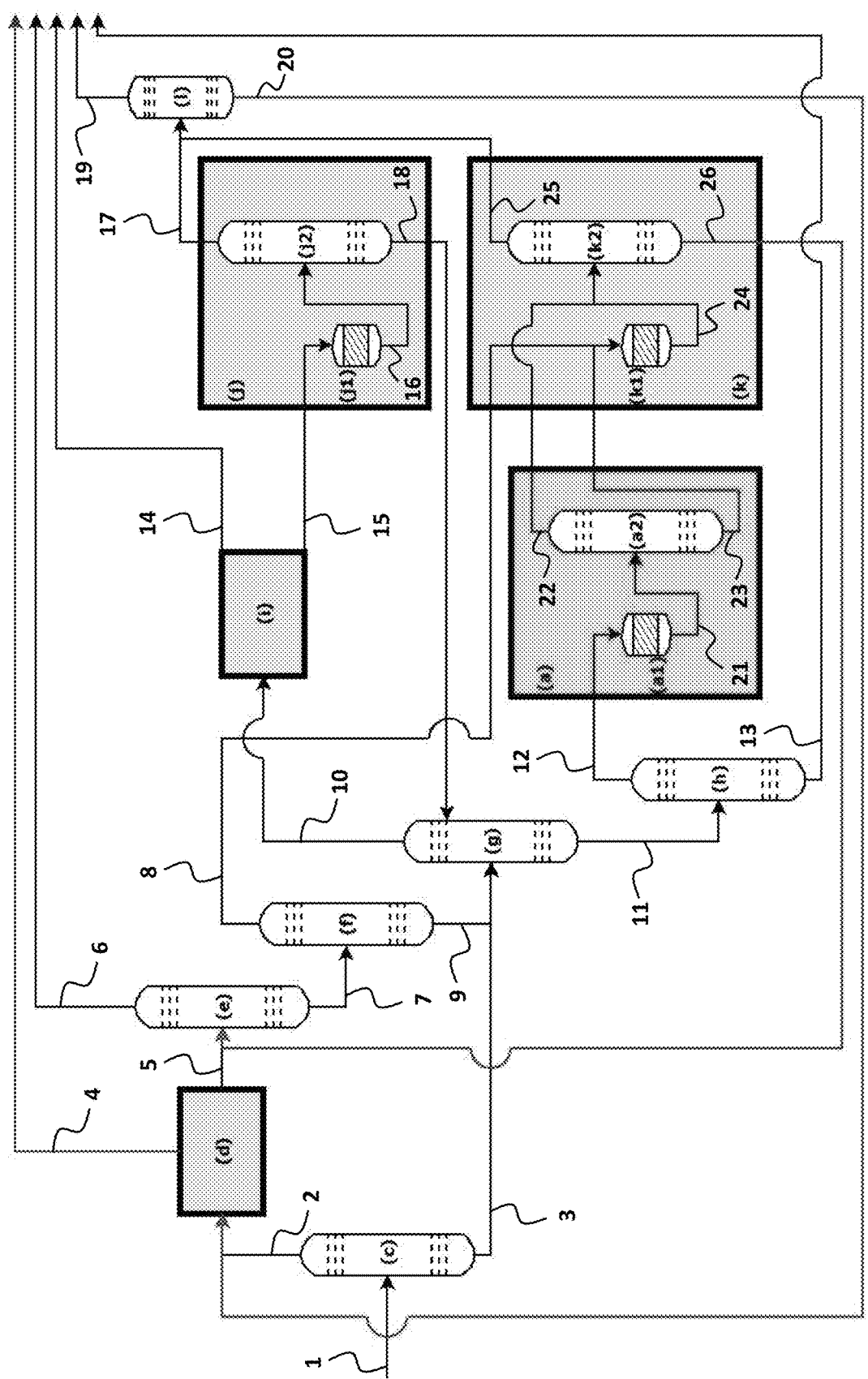
FIG. 2 according to the invention is a more detailed view of the hydrogenolysis unit (a) integrated in an aromatic complex having a reformate splitter (c), a unit for the extraction of benzene and toluene (d), a unit for the extraction of aromatics (i), a fractionation train consisting of the columns (e), (f), (g) and (h), an isomerization unit (j1) and a transalkylation unit (k1).

In the continuation of the text, the notations of FIG. 2 are used to designate the different units.

In fact, the selective hydrogenolysis unit (a) comprises the reaction section (a1) and the column for separation of the effluents (a2). In the same way, the isomerization unit (i) comprises the reaction section (i1) and the column for separation of the effluents (i2). The transalkylation unit (k) comprises the reaction section (k1) and the column for separation of the effluents (k2).

In the context of the present invention, the unit for the selective hydrogenolysis (a1) of the alkylaromatics can advantageously be coupled with an "aromatic complex" unit, the purpose of which is to produce xylenes or some of their isomers (para-xylene in particular) and benzene.

The selective hydrogenolysis unit (a1) then exchanges streams with the aromatic complex. Generally, the aromatic complex is fed with hydrocarbon fractions containing predominantly atoms, the carbon number of which extends from 6 to 10.

Several configurations are then possible:
  The selective hydrogenolysis unit (a1) is used as pretreatment upstream of the aromatic complex. In this case, external streams can directly feed it (example 6 to 10 carbon reformate, A9/A10 fraction, and the like) and the effluents are then directed to the aromatic complex.
  The selective hydrogenolysis unit (a1) treats one or more fraction(s) internal to the complex. In this case, it is in part or completely fed with one or more streams originating from the aromatic complex, mainly the stream containing aromatics having 9 and 10 carbon atoms resulting from the fractionation train of the aromatic complex. The effluents are then also returned to the aromatic complex.
  The combination of the two configurations is also possible and remains within the scope of the present invention.

In all cases, the effluents are then enriched in methyl groups. They are sent, in all or part, to the aromatic complex in order to produce xylenes and benzene. Overall, as will be shown in the examples below, the integration of the selective hydrogenolysis unit into the aromatic complex increases the production of para-xylene to the detriment of the production of benzene.

Examples According to the Invention

Example 1 illustrates the performance qualities of a selective hydrogenolysis unit in which an aromatic fraction having mainly 9 carbon atoms is treated, the composition by weight of which fraction is described in detail in table 1 below.

TABLE 1

| Composition by weight of the feedstock of the selective hydrogenolysis unit | | |
|---|---|---|
| A8 | | 1.5 |
| A9 | Total | 96.7 |
| | Trimethylbenzene | 54.4 |
| | Methyl(ethyl)benzene | 36.6 |
| | Others | 5.8 |
| A10 | | 1.7 |
| Nonaromatic | | 0.1 |

The selective hydrogenolysis unit operates under the following conditions:
  Liquid feedstock flow rate: 191.4 g/h
  Catalyst: 12.8 g, 10% Ni/alumina of δ type catalyst
  Pressure of the reactor: 4.5 bar
  Temperature of the reactor: 370° C.
  Hydrogen coverage: 3.1 moles of $H_2$ per mole of hydrocarbons The performance qualities of the test are presented in table 2 below. Focus is directed on the molar flow rates of nuclei and alkyl groups. The gain in methyl groups is a little more than 2%, showing the advantage of the selective hydrogenolysis unit as described in the present invention.

TABLE 2

| Characteristics of the feedstock and of the effluents | | |
|---|---|---|
| | Feedstock [mol/h] | Effluent [mol/h] |
| Nucleus | 1.663 | 1.662 |
| Methyl | 3.399 | 3.476 |
| Ethyl | 0.616 | 0.351 |
| Propyl | 0.083 | 0.038 |
| Butyl | 0.017 | 0.005 |

Example 2 illustrates a scenario where the selective hydrogenolysis unit treats an A9/A10 fraction internal to the aromatic complex, because this fraction is rich in alkylbenzenes with alkyl chains having more than two carbons (positional isomers of propylbenzenes, methyl(ethyl)benzenes, butylbenzenes, methyl(propyl)benzenes, dimethyl (ethyl)benzenes and diethylbenzenes).

This fraction is extracted at the top of the heavy aromatics separation column, which generally feeds the transalkylation unit.

The hydrogenolysis unit according to the present invention can be seen as a unit for pretreatment of the A9+ fraction upstream of the transalkylation unit.

The hydrogenolysis unit produces a broad aromatic fraction (from 6 to 10 carbon atoms). These effluents contain xylenes which it is necessary to extract before feeding the transalkylation unit. This is because this unit is at thermodynamic equilibrium and produces xylenes by A9+/A7 transalkylation. It is thus necessary to extract the xylenes in order not to penalize the conversion. The solution chosen consists in separating the effluents into an A9+ fraction (feeding the transalkylation) and an unstabilized A8− fraction which benefits from the existing fractionation train in order to be stabilized and to separate the A6/A7/A8 aromatics.

In the present example, illustrated by FIG. 2, the aromatic complex is nonlimitingly composed:
  of a unit (d) for extraction of benzene and toluene (a separation by solvent extraction of the aliphatic compounds from benzene and toluene),
  of a unit (i) for extraction of para-xylene from the other A8 compounds (meta-xylene, ortho-xylene, ethylbenzene),
  of a unit (j1) for isomerization of xylenes and for dealkylation of ethylbenzene,
  of a unit (a1) for selective hydrogenolysis of the A9/A10 fraction which operates under the following conditions:
    Catalyst: 10% Ni/alumina of δ type catalyst
    Pressure of the reactor: 3.5 bar
    Temperature of the reactor: 410° C.
    Hydrogen coverage: 3.0 moles of $H_2$ per mole of hydrocarbons
    HSV: 10 $h^{-1}$ of a unit (k) for transalkylation of toluene, trimethylbenzenes and tetramethylbenzenes.

The reformate, stream (1), feeds the column for separation (c) of the reformate, which makes it possible to separate a C7− fraction, stream (2), and an A8+ fraction, stream (3). The C7− fraction, stream (2), mixed with the stream (20) originating from the stabilization column (l), feeds the unit (d) for extraction of the aromatics in order to extract the aliphatic entities from the C6 and C7 aromatics. The C6/C7 raffinate, stream (4), is directly exported as a coproduct from the complex. The benzene/toluene fraction, stream (5), called extract from the unit for the extraction of the aromatics, is mixed with the stream (26) originating from the separation column (k2) and feeds the main fractionation train.

The main fractionation train of the aromatic complex is composed of 4 columns:

Benzene column (e) (fed with the extract from the unit for the extraction of the aromatics, stream (5), and the benzene/toluene fraction, stream (26), originating from the separation column (l)). It produces benzene at the top, stream (6), which is one of the products desired at the outlet of the aromatic complex. At the bottom, the aromatics having more than 7 carbon atoms, stream (7), are extracted.

Toluene column (f) fed via the bottom of the benzene column, stream (7). At the top, the toluene, stream (8), is exported to the transalkylation unit (k) while the bottom product, stream (9), is mixed with the bottom product from the column (c) for separation of the reformate, stream (3), in order to feed the xylenes column (g).

Xylenes column (g), also fed with the isomerate originating from the isomerization unit (j). At the top, the A8 fraction, stream (10), feeds the unit (i) for extraction of para-xylene. The A9+ fraction, stream (11), is extracted at the column bottom.

Heavy aromatics column (h): in order to limit the content of naphthalene, which is a precursor of coke in catalytic units, the A9+ fraction, stream (11), is tailed in the column (h). At the top, monoaromatics having 9 and 10 carbon atoms, stream (12), are recovered. The compounds having a higher boiling point are extracted at the column bottom and exported as coproducts, stream (13).

The A8 fraction, stream (10), is treated in the unit (i) for extraction of para-xylene.

para-Xylene, stream (14), is exported as main product. The extract from this unit, composed of ortho-xylene, meta-xylene and ethylbenzene, stream (15), feeds the isomerization unit (j). In the reaction section (j1), the isomers of para-xylene are isomerized while ethylbenzene is dealkylated to produce benzene. The effluents from the isomerization reaction section, stream (16), are stabilized and separated. The separation column (j2) makes it possible to extract the isomerate, stream (18), at the bottom. This isomerate is enriched in para-xylene and returns to the xylenes column (g) while the unstabilized C7− fraction, stream (17), is stabilized in the stabilization column (l) after mixing with the stream (25) originating from the transalkylation unit. The stabilized benzene/toluene fraction, stream (20), is recycled at the inlet of the unit (d) for extraction of the aromatics.

The aromatic complex is composed of a loop for the conversion of toluene and aromatics having 9 and 10 carbon atoms. The A9/A10 fraction, stream (12), originating from the top of the heavy aromatics column (h) is treated in the selective hydrogenolysis unit (a). The C2+ alkyls are in part converted into methyls. The aromatics are thus in part converted into aromatics having a lower carbon number. The stream (21), corresponding to the effluents from the selective hydrogenolysis reaction section (a1), is separated in the separation column (a2) into a C8− fraction, stream (22), and an A9+ fraction, stream (23).

The C8− fraction, stream (22), bypasses the transalkylation reaction section in order to feed the downstream stabilization stage.

The A9+ fraction, stream (23), mixed with the toluene, stream (8), originating from the top of the toluene column (f), feeds the transalkylation unit (k). This unit produces xylenes by transalkylation of aromatics deficient in methyl groups (toluene) and aromatics having an excess of methyl groups (tri- and tetramethylbenzene).

The effluents from the transalkylation unit, stream (24), are then separated in the separation column (k2). A part of the benzene and the more volatile entities are extracted at the top of the column (k2), stream (25), and then sent to the stabilization column (l). The heavy fraction of the effluents, stream (26), composed of aromatics having more than 6 carbon atoms, is recycled to the benzene column (e), the first stage of the main fractionation.

According to the prior art, that is to say without a selective hydrogenolysis unit, the A9/A10 fraction, stream (12), produced at the top of the heavy aromatics column (h) is sent directly to the transalkylation unit (k). In this scenario, the transalkylation unit also makes it possible to hydrodealkylate the long alkyls (terminal cleavage of ethyls, propyls and butyls flush with the aromatic nucleus).

The reformate, stream (1), feeding the complex has the composition represented in table 3 below.

The total flow rate by weight of aromatics is 217.4 t/h.

TABLE 3

Distribution by weight of the aromatics contained in the reformate feeding the aromatic complex

| Benzene | | 4.7% |
|---|---|---|
| Toluene | | 17.8% |
| A8 | | 31.3% |
| A9 | Trimethylbenzene | 17.3% |
| | Others | 15.5% |
| A10 | Tetramethylbenzene | 2.9% |
| | Others | 10.4% |

The comparison between the reference case and the performance qualities of the aromatic complex with a unit for the selective hydrogenolysis of the alkylaromatics according to the invention is presented in table 4 below.

TABLE 4

Comparison of the products of the aromatic complex between the reference case (state of the art) and a scheme in accordance with the invention

| | Reference | Invention |
|---|---|---|
| Benzene (t/h) | 36.8 | 29.4 |
| para-Xylene (t/h) | 160 | 168.5 |

The hydrogenolysis unit coupled to the aromatic complex makes possible, in the case presented, a gain in para-xylene production of the order of 5%, which is particularly advantageous in the current context of petrochemistry.

The invention claimed is:

1. A selective hydrogenolysis process in which a feedstock rich in aromatic compounds having more than 8 carbon atoms is treated and which process comprises converting one or more alkyl group(s) having at least two carbon atoms attached to a benzene nucleus into one or more methyl group(s) to increase the amount of available methyl groups and consequently to produce xylenes to the detriment of benzene, said process being carried out in a reactor in the presence of a catalyst consisting of nickel nanoparticles deposited on alumina or silica, and having or not having structured porosity, the reaction taking place:
    at a temperature of between 300° C. and 550° C.,
    at a pressure of between 1 and 30 bar,
    with a $H_2$/HC molar ratio of between 1 and 10, and
    with a weight hourly space velocity of between 0.1 and 50 $h^{-1}$.

2. The selective hydrogenolysis process as claimed in claim 1, which takes place in a reactor that is a fixed bed type reactor and the catalyst is in the form of extrudates.

3. The selective hydrogenolysis process as claimed in claim 1, which takes place in a reactor that is a moving bed type reactor and the catalyst is in the form of approximately spherical beads.

4. The selective hydrogenolysis process as claimed in claim 1, wherein the hydrocarbon feedstock contains more than 80% by weight of aromatics, and at least 90% by weight of molecules having between 8 and 10 carbon atoms.

5. The selective hydrogenolysis process as claimed in claim 1, in which the reaction takes place:
    at a temperature of between 370° C. and 450° C.,
    at a pressure of between 2 and 10 bar,
    with a $H_2$/HC molar ratio of between 1.5 and 6, and
    with a weight hourly space velocity of between 3 and 20 $h^{-1}$.

6. The selective hydrogenolysis process as claimed in claim 1, in which the reaction takes place:
    at a pressure of between 2 and 4.5 bar.

7. The selective hydrogenolysis process as claimed in claim 1,
wherein the reaction takes place:
    at a temperature of between 350° C. and 500° C.,
    at a pressure of between 2 and 20 bar,
    with a $H_2$/HC molar ratio of between 1.5 and 6, and
    with a weight hourly space velocity of between 1 and 30 $h^{-1}$.

8. A process for the production of xylenes using an aromatic complex comprising a selective hydrogenolysis process as claimed in claim 1, said aromatic complex comprising at least:
    a unit for the hydrogenolysis (a) of alkylaromatics in which aromatics having between 9 and 10 carbon atoms, imported or extracted from internal streams of the aromatic complex, are treated,
    a unit of transalkylation type (k) in which toluene and trimethylbenzenes are converted into xylenes,
    a fractionation train formed at least of a benzene separation column (e), a toluene separation column (f), a xylenes separation column (g) and a heavy aromatics separation column (h), wherein the fractionation train extracts benzene, toluene and the xylenes from a reformate stream (1) comprising compounds having at least 6 carbon atoms;
wherein:
    an aromatic fraction having 9 and 10 carbon atoms (12) resulting from the heavy aromatics separation column (h) is fed to the hydrogenolysis unit (a),
    the effluents of the hydrogenolysis unit (a) are sent to the transalkylation unit (k), and
    a bottom fraction (26) having 8 and more carbon atoms of the transalkylation unit (k) is sent to the fractionation train.

9. The process for the production of xylenes as claimed in claim 8, in which:
    the fractionation train comprises columns for distillation of the aromatics and separates the following 5 fractions:
    a benzene fraction (6),
    a toluene fraction (8),
    an aromatic fraction having 8 carbon atoms (10),
    an aromatic fraction having 9 and 10 carbon atoms (12), and
    a heavy aromatics fraction (13), the most volatile entities of which are aromatics having 10 carbon atoms,
    and
    the hydrogenolysis unit (a) treats the aromatic fraction having 9 and 10 carbon atoms (12) resulting from the fractionation train, the hydrogenolysis effluent being passed to a first separation column (a2) to provide a heavy fraction (23) having at least 9 carbon atoms, which is mixed with the toluene fraction (8) resulting from the fractionation train to provide a mixture, which is fed to the transalkylation unit (k), the transalkylation effluent being passed to a second separation column (k2) to provide:
    a bottom fraction (26) having more than 6 carbon atoms, which is recycled to the benzene separation column (e) of the fractionation train; and
    a stream (25) comprising benzene and compounds more volatile than benzene that is sent to a unit (d) for extraction of benzene and toluene from which a benzene/toluene fraction (5) is recycled to the benzene separation column (e) of the fractionation train.

10. The process for the production of xylenes as claimed in claim 8, in which:
    the fractionation train comprises columns for distillation of the aromatics and separates the following 5 fractions:
    a benzene fraction (6),
    a toluene fraction (8),
    an aromatic fraction having 8 carbon atoms (10),
    an aromatic fraction having 9 and 10 carbon atoms (12), and
    a heavy aromatics fraction (13), the most volatile entities of which are aromatics having 10 carbon atoms,
    and
    the hydrogenolysis unit (a) treats the aromatic fraction having 9 and 10 carbon atoms (12) resulting from the fractionation train and an imported feedstock rich in alkylaromatics, the hydrogenolysis effluent being passed to a first separation column (a2) to provide:
    a heavy fraction (23) having at least 9 carbon atoms which is mixed with the toluene fraction resulting from the fractionation train to provide a mixture which is fed to a transalkylation section (k1) of the transalkylation unit (k); and
    a light fraction (22) having 8 and fewer carbon atoms bypassing the transalkylation section (k1) to feed a downstream separation column (k2) of the transalkylation unit (k).

11. The process for the production of xylenes as claimed in claim 9, in which the aromatic fraction having 8 carbon atoms (10) is treated in a unit for the extraction of paraxylene (i).

12. The process for the production of xylenes as claimed in claim 11, in which the unit for the extraction of para-xylene (i) is of simulated moving bed type in which separation is by molecular sieve and desorbent.

13. The process for the production of xylenes as claimed in claim 11, in which raffinate from the unit for the extraction of para-xylene (i), formed of ortho-xylene, meta-xylene and ethylbenzene, is converted in an isomerization unit (j) targeted at producing para-xylene, wherein the effluents of the isomerization unit (j) being recycled to the fractionation train.

14. A process for the production of xylenes using an aromatic complex comprising a selective hydrogenolysis process in which a feedstock rich in aromatic compounds having more than 8 carbon atoms is treated and which comprises converting one or more alkyl group(s) having at least two carbon atoms attached to a benzene nucleus into one or more methyl group(s) to increase the amount of available methyl groups and consequently to produce xylenes to the detriment of benzene, said selective hydrogenolysis process being carried out in a reactor in the presence of a catalyst comprising at least one metal from Group VIII of the Periodic Table, and a porous support comprising at least one crystalline or noncrystalline refractory oxide, having or not having structured porosity, the selective hydrogenolysis reaction taking place:

at a temperature of between 300° C. and 550° C.,
at a pressure of between 1 and 30 bar,
with a $H_2$/HC molar ratio of between 1 and 10, and
with a weight hourly space velocity of between 0.1 and 50 $h^{-1}$, wherein the aromatic complex comprises at least:
a unit for the hydrogenolysis (a) of alkylaromatics in which aromatics having between 9 and 10 carbon atoms, imported or extracted from internal streams of the aromatic complex, are treated,
a unit of transalkylation type (k) in which toluene and trimethylbenzenes are converted into xylenes, and
a fractionation train formed at least of a benzene separation column (e), a toluene separation column (f), a xylenes separation column (g) and a heavy aromatics separation column (h), the fractionation train extracting benzene, toluene and the xylenes from a reformate stream (1) comprising compounds having at least 6 carbon atoms, and wherein:
the fractionation train comprises columns for distillation of the aromatics which make it possible to separate the following 5 fractions:
a benzene fraction (6),
a toluene fraction (8),
an aromatic fraction having 8 carbon atoms (10),
an aromatic fraction having 9 and 10 carbon atoms (12), and
a heavy aromatics fraction (13), the most volatile entities of which are aromatics having 10 carbon atoms,
and
the hydrogenolysis unit (a) treats the aromatic fraction having 9 and 10 carbon atoms (12) resulting from the fractionation train, the hydrogenolysis effluent being passed to a first separation column (a2) to provide:
a heavy fraction (23) having at least 9 carbon atoms which is mixed with the toluene fraction resulting from the fractionation train to provide a mixture which is fed to a transalkylation section (k1) of the transalkylation unit (k); and
a light fraction (22) having 8 and fewer carbon atoms bypassing the transalkylation section (k1) to feed a downstream separation column (k2) of the transalkylation unit (k).

15. The process according to claim 14, wherein the hydrogenolysis unit (a) treats the aromatic fraction having 9 and 10 carbon atoms (12) resulting from the fractionation train and an imported feedstock rich in alkylaromatics.

16. The selective hydrogenolysis process as claimed in claim 14, wherein the reaction takes place:
at a temperature of between 370° C. and 450° C.,
at a pressure of between 2 and 10 bar,
with a $H_2$/HC molar ratio of between 1.5 and 6, and
with a weight hourly space velocity of between 3 and 20 $h^{-1}$.

* * * * *